United States Patent [19]

Bailey et al.

[11] 3,959,461

[45] May 25, 1976

[54] HAIR CREAM RINSE FORMULATIONS CONTAINING QUATERNARY AMMONIUM SALTS

[75] Inventors: August V. Bailey; Gene Sumrell, both of New Orleans, La.

[73] Assignee: The United States of America as represented by the Secretary of Agriculture, Washington, D.C.

[22] Filed: May 28, 1974

[21] Appl. No.: 473,477

[52] U.S. Cl. ............................ 424/70; 252/155; 252/541; 252/547; 260/404.5; 424/365
[51] Int. Cl.² ........................................ A61K 7/08
[58] Field of Search .................... 424/70, 329; 260/567.6 M, 404.5, 567.6 P; 252/155, 541, 547

[56] References Cited
UNITED STATES PATENTS

| | | | |
|---|---|---|---|
| 2,928,772 | 3/1960 | Anderson | 424/70 |
| 3,069,320 | 12/1962 | Vitalis | 424/329 X |
| 3,272,712 | 9/1966 | Kalopissis | 424/70 |
| 3,423,504 | 1/1969 | Birkelo et al. | 424/70 |

*Primary Examiner*—Sam Rosen
*Assistant Examiner*—Vera C. Clarke
*Attorney, Agent, or Firm*—M. Howard Silverstein; Salvadore J. Cangemi

[57] ABSTRACT

New quaternary ammonium salts have been prepared from an amino amide and an amino ester and found to be useful in hair cream rinse formulations.

3 Claims, No Drawings

HAIR CREAM RINSE FORMULATIONS CONTAINING QUATERNARY AMMONIUM SALTS

FIELD TO WHICH THIS INVENTION RELATES

Quaternary ammonium compounds will exhibit markedly different properties depending upon the substituent non-hydrophobic groups on the nitrogen atom. It is a fact that many of the patented cationic surface active agents differ among themselves solely in the nature of the non-hydrophobic substituents on the nitrogen atom. The usual procedure in making quaternary ammonium compounds is to react a tertiary amine with an alkyl halide to form the salt. These compounds have high surface activity. Similarly the hydrophobic group can be joined to the cationic group through an intermediate linkage such as an ester or an amide. In these compounds the hydrophobic group is considered to be contained in the fatty acid group which forms the amide or ester linkage while variations in chain length and/or structure of the intermediate can have some interesting effects on the surface activity of the compounds.

This invention relates to the manufacture of new quaternary ammonium compounds prepared from an amino amide and an amino ester. More specifically, it relates to the quaternary ammonium compounds of the structures

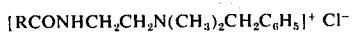

and

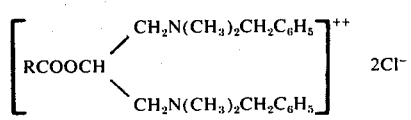

where "R" is a saturated normal alkyl group of at least 11 carbon atoms and consists of treating an unsymmetrical alkyl diamine or an alkanolamine with an acid chloride and reacting the resulting product with an alkylating agent such as benzyl chloride.

The new products have pronounced surface active properties in aqueous solution and are useful for inclusion in hair cream rinse formulations.

The following examples illustrate but do not limit the scope of the invention.

EXAMPLE 1

Eighty-eight parts of unsymmetrical dimethylethylenediamine is combined with 275 parts of palmitoyl chloride in the presence of 110 parts of triethylamine. The product, N,N-dimethylaminoethylpalmitamide, was recovered by filtration removal of the triethylamine hydrochloride salt formed followed by elution through an activated alumina column in a chloroform solution for removal of free acid. After stripping off the chloroform, 227 parts of the product was then combined with 140 parts of benzyl chloride. Interaction of the amino amide and the benzyl chloride yields a crystalline product which dissolves easily in water.

EXAMPLE 2

One hundred forty-six parts of 1,3-bis-N,N-dimethylamino-2-propanol is combined with 275 parts of palmitoyl chloride in the presence of 110 parts of triethylamine. The product, 1,3-bis-N,N-dimethylamino-2-propyl palmitate, was recovered by filtration removal of the triethyl amine hydrochloride salt formed followed by elution through an activated alumina column in chloroform solution for removal of free acid. After stripping off the chloroform, 236 parts of the product when combined with 280 parts of benzyl chloride yields a solid mass of soapy consistancy which dissolves easily in water.

EXAMPLE 3

In accordance with the present invention, an aqueous cream rinse of good foaming character was prepared by combining 2 parts of lanolin, 3 parts of cetyl alcohol, 85 parts of water and 10 parts of the new quaternary ammonium salt of the structure

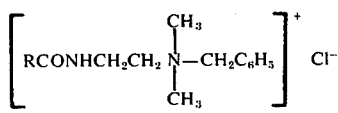

wherein "R" is a saturated normal alkyl group of about 11 to 21 carbon atoms. When applied to human hair following shampooing, the hair was left with good luster, ease of manageability, and without tangles and snarls normally associated with wet hair.

The usual foam builders or stabilizers, thickeners, and lipophilic materials can be added to or substituted into the basic formulation for specific effects.

EXAMPLE 4

In accordance with the present invention, an aqueous cream rinse of good foaming character was prepared by combining 2 parts of lanolin, 3 parts of cetyl alcohol, 85 parts of water and 10 parts of the new quaternary ammonium salt of the structure:

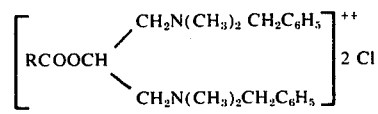

wherein "R" is a saturated normal alkyl group of about 11 to 21 carbons. When applied to human hair following shampooing the hair was left with good luster, ease of manageability and without tangles and snarls normally associated with wet hair.

The usual foam builders or stabilizers, thickeners, and lipophilic materials can be added to or substituted into the basic formulation for specific effects.

We claim:
1. A hair cream rinse formulation comprising two parts of lanolin, three parts of cetyl alcohol, 85 parts of water, and 10 parts of a quaternary ammonium salt selected from the group consisting of

and

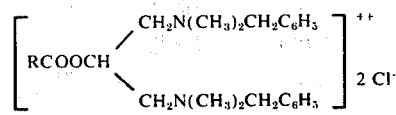

wherein R is a saturated normal alkyl group of about 11 to 21 carbon atoms.
2. The formulation according to claim 1 wherein the quaternary salt is:
[C$_{15}$H$_{31}$CONHCH$_2$CH$_2$N(CH$_3$)$_2$CH$_2$C$_6$H$_5$]$^+$ Cl$^-$
3. The formulation according to claim 1 wherein the quaternary salt is:
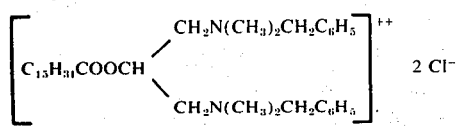
* * * * *